May 30, 1950 P. J. HOWARD Plant Pat. 944
ROSE PLANT
Filed March 4, 1949
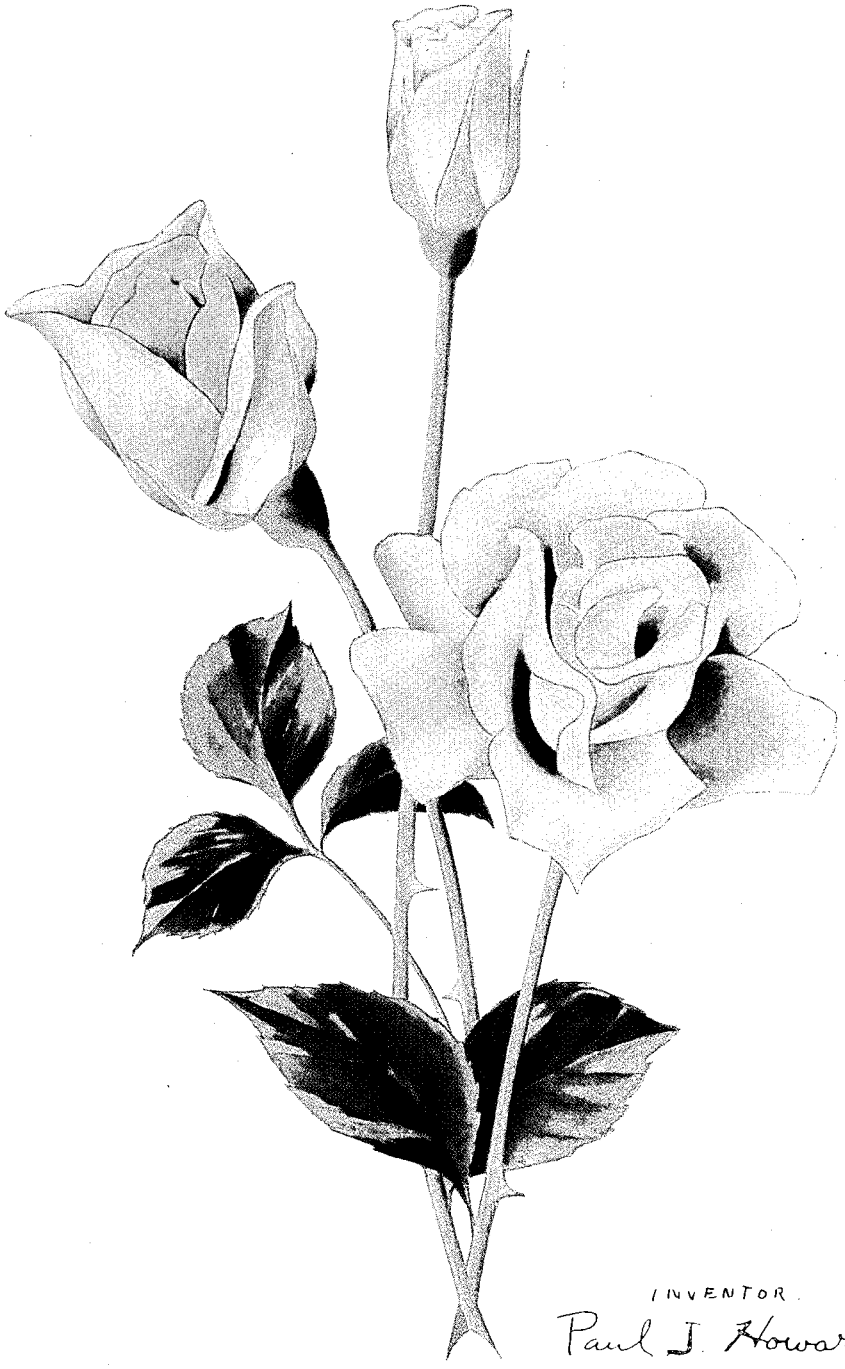
INVENTOR.
Paul J. Howard
By Orville M. Kile
Plant Patent Agt Patented May 30, 1950

UNITED STATES PATENT OFFICE

944

ROSE PLANT

Paul J. Howard, Los Angeles, Calif., assignor to Paul J. Howard California Flowerland, Los Angeles, Calif., a corporation Application March 4, 1949, Serial No. 79,641

1 Claim. (Cl. 47—61)

My present invention pertains to a new and distinct variety of hybrid tea rose plant, resulting from a cross between the varieties "California" (Plant Patent No. 449) and "Eternal Youth" (Plant Patent No. 332).

The variety is distinguished particularly by the unusual color of its flowers which differs radically from the color of the flowers of either parent. The principal color would popularly be called cerise or cherry red in the bud and early flower stages, while the open flowers are lighter tones of the same color which do not blue or fade. This bright color contrasts with the vivid yellow aiglet and darker yellow stamens of the open flower.

The form of the flower also differs radically from that of either parent, and in the fully open stage considerably resembles the floribundas with open centers, although exceeding the latter in size. Fragrance of the new variety is a more spicy type than that of either parent.

Its growth and foliage characteristics are much like those of its parent, "California," and like this variety is notable for its profuse and continuous blooming habit.

My new variety has been asexually reproduced for several years, by means of budding in our nurseries in Los Angeles, and its characteristics appear to be permanent.

The original illustrations accompanying these specifications show three specimens of the flower in various stages of opening, together with portions of stems and foliage—all in approximately their true colors.

Following is a detailed description of this new variety. Color plates refer to Ridgway's Color Standards and Nomenclature, except where otherwise indicated.

*The plant*

Form: Upright bush.

Growth: Vigorous. Attains a height of 3 to 4 feet.

Blooming habit: Profuse and continuous bloomer.

Stems: Sturdy and stiff. Color approximately Grass Green (Plate VI), with deep bronze overlay. *Thorns*—stems have many thorns, particularly toward base of stem. They are medium to large in size, very sharp, red, and outward-pointing.

Foliage:

*Leaflets.*—Three to five.

*Color.*—Very dark green, between Dark Dull Yellow Green and Empire Green (Plate XXXII).

*Size.*—Small to medium.

*Quantity.*—Moderate.

*Shape.*—Oval with sharp acuminate point.

*Edge.*—Almost entire, with very fine serrations.

*Texture.*—Heavy and leathery.

*Aspect.*—Smooth and waxy.

*Rachis.*—Smooth.

*Stipules.*—Narrow; clinging.

*The flower*

Bud:

*Size.*—Medium, approximately 1½ inches long.

*Shape.*—Long, pointed.

*Opening.*—Slow and unaffected by adverse weather conditions.

*Sepals.*—Usually simple, sometimes with slight tendency to be foliaceous and branched. Edges smooth. Light green, approximately Courge Green (Plate XXXI) on outside, bronzed on side next sun. Inside Absinthe Green (Plate XXXI).

*Peduncle.*—Mostly smooth; bronzed where exposed to sun.

Bloom:

*Borne.*—Singly.

*Size.*—Medium, averaging 3½ to 4 inches when fully open.

*Form.*—High centered, opening to cup shape when it usually displays a large number of stamens.

*Petalage.*—Double, with 14 to 20 petals.

*Color.*—The color of the flower is novel and cannot be accurately described in comparison with Ridgway's Color Standards. The general color effect of the opening bud is a rich, intense cherry red, approximately the color of Plate No. 722 of the Horticultural Color Chart. The open flowers are lighter tones of cherry red and even as light as Deep Rose Pink (Plate XII, Ridgway's), with a rather large aiglet of Light Cadmium (Plate IV, Ridgway's) which is more prominent on the inner surface of the petal, and which suffuses upward into the cherry color.

Petals:

*Texture.*—Medium.

*Aspect.*—Silky.

*Form.*—Oval, without quilling or rolling.

*Fragrance.*—Spicy.

*Persistence.*—Drop off cleanly.

*Lasting quality.*—Good, both on plant and as cut flower.

Reproductive organs:

*Pistils.*—Many, short, bunched in center of flower. *Styles*—red; *stigmas*—light yellow.

*Stamens.*—Many, curved in cup shape; uneven in length, up to approximately 1 inch. *Filaments*—Apricot Yellow (Plate IV); *anthers*—medium in size, Light Orange Yellow (Plate III), turning to light brown after flower opens.

Having thus disclosed my invention, I claim:

The new and distinct variety of hybrid tea rose plant, substantially as herein shown and described, characterized particularly by its profuse and continuous blooming habit, its vigorous upright growth, its bronzed stems, and its flowers with loose open form, spicy fragrance, and cherry red color which does not turn blue with age.

PAUL J. HOWARD.

No references cited.